United States Patent [19]

Huang

[11] Patent Number: 5,259,938
[45] Date of Patent: Nov. 9, 1993

[54] PROCESS FOR OMEGA-HALO-PERFLUORO ACID CHLORIDES

[75] Inventor: Hsu-Nan Huang, Newark, Del.

[73] Assignee: E. I. Du Pont de Nemours and Company, Wilmington, Del.

[21] Appl. No.: 944,673

[22] Filed: Sep. 15, 1992

[51] Int. Cl.$^5$ .................................... C07C 51/00
[52] U.S. Cl. ..................... 204/157.87; 204/157.94; 204/158.11
[58] Field of Search ........... 204/157.6, 157.94, 158.11, 204/157.89

[56] References Cited

U.S. PATENT DOCUMENTS

| Re. 29,044 | 11/1976 | Konno et al. | 204/157.89 |
| 3,151,051 | 9/1964 | Brald et al. | 204/158 |
| 4,022,824 | 5/1977 | Childs | 260/539 A |

FOREIGN PATENT DOCUMENTS 60-78935  5/1985  Japan .

*Primary Examiner*—T. Tung
*Assistant Examiner*—Cybille Delacroix-Muirheid

[57] ABSTRACT

A liquid phase process for preparing ω-haloperfluoroacid chlorides by the photo oxidation of polyfluoroalkyl mono- and di-chloromethanes in the presence of chlorine using light wavelengths greater than 280 nm.

6 Claims, No Drawings

PROCESS FOR OMEGA-HALO-PERFLUORO ACID CHLORIDES

FIELD OF THE INVENTION

This invention relates to a liquid phase process for preparing ω-haloperfluoro acid chlorides by the photochemical catalyzed oxidation of polyfluoroalkyl mono- and di-chloromethanes in the presence of chlorine using light of wavelengths greater than 280 nm.

DESCRIPTION OF THE RELATED ART

Perfluoro acid chlorides and ω-chloro-perfluoro acid chlorides are useful as starting materials for the synthesis of agricultural chemicals, pharmaceuticals, surfactants and repellents, since as the acid chloride they readily react with amines or alcohols to produce amides or esters, respectively, having unique properties due to the presence of the perhalo groups. These groups can influence solubility, repellency, wettability of products resulting in a variety of different properties depending on the nature of the halo group and the length of the carbon chain.

U.S. Pat. No. 3,883,407, discloses the oxidation of anhydrous 1,1-dichloro-2,2,2-trifluoroethane with oxygen in the gas phase at temperatures up to 250° C., in the presence of ultraviolet radiation to produce trifluoroacetyl chloride. Further it is stated that the ultraviolet radiation catalyzed, liquid phase reaction is unsuitable commercially since HF is apparently produced which attacks the glass or quartz light wells.

Haszeldine and Nyman in *Journal of the Chemical Society* 1959 p. 387 ff. disclose the preparation of trifluoroacetyl chloride by the photo oxidation of various chlorofluoroethanes. With 1,1-dichloro-2,2,2-trifluoroethane there was always about 20% of trifluoroacetic acid formed along with the trifluoroacetyl chloride. In addition the space-time yields of the product were so low as not to be suitable for a commercial process and the details were sketchy.

SUMMARY OF THE INVENTION

The present invention relates to an improvement in the photochemical oxidation process for the preparation of ω-haloperfluoroacid chlorides by the liquid phase oxidation of compounds of the general formula $M(CF_2)_nCH_xCl_y$, wherein $n=1-10$, $x=1$ or $2$, $x+y=3$ and $M=F$ or $Cl$.

The liquid phase oxidation is carried out with molecular oxygen using chlorine as an initiator (and as a reagent when x equals 2) in the presence of light at wavelengths greater than 280 nm. The use of wavelengths greater than 280 nm prevents the considerable etching of the glass light well and other glass equipment observed when standard high or medium pressure mercury vapor lamps are used. In this manner, ω-haloperfluoro acid chlorides may be obtained in good yield without significant corrosion of the glass light well or reactor, which is desirable for a commercial process.

DETAILED DESCRIPTION OF THE INVENTION

The present invention relates to an improvement in the photochemical oxidation process for the preparation of ω-haloperfluoroacid chlorides by the liquid phase oxidation of compounds of the general formula $M(CF_2)_nCH_xCl_y$, wherein $n=1-10$, $x=1$ or $2$, $x+y=3$ and $M=F$ or $Cl$. In general, the reactions are thought to occur according to the following equations:

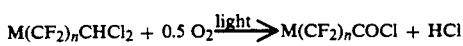

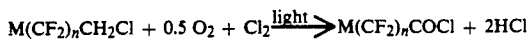

Liquid phase photo oxidation of compounds of the formula $M(CF_2)_nCH_xCl_y$ wherein $n=1-10$, $M=Cl$ or $F$, $x=1$ or $2$ and $x+y=3$, is desirable since: (1) solvent may be used as a diluent for safety considerations (i.e. the use of a solvent allows more convenient temperature control and allows for convenient operation outside of the explosive range of the reactants); (2) less volatile compounds of the formula $M(CF_2)_nCH_xCl_y$ may be photooxidized; and, (3) the space time yield is improved. The prior art states that in the liquid phase some HF is apparently produced which attacks the glass or quartz light wells, thus requiring considerable reactor maintenance or the use of expensive HF resistant materials. The normal wavelength range of radiation from a light source such as a high or medium pressure mercury vapor lamp is from 200–600 nm. The radiation of wavelength less than 280 nm leads to the formation of side products, particularly hydrogen fluoride which corrodes, i.e., etches the glass or quartz light well and other glass components of the reactor, making the process less efficient and economically unattractive. It has now been found that the oxidation can be carried out at wavelengths greater than 280 nm when controlled amount of chlorine is added to the reaction solution. In this manner ω-haloperfluoro acid chlorides may be obtained in good yield, without significant corrosion of the glass light well or reactor, which is desirable for a commercial process. The present process is further commercially feasible since the material compatibility problem is solved by minimizing HF formation and lowering 1,1,1-trichloro-2,2,2-trifluoroethane, F-113a formation.

In general the reaction may be carried out with or without solvent, and as a batch or continuous process. The reactant of formula $M(CF_2)_nCH_xCl_y$ and any solvent is charged into a photochemical reactor. The reactor contents are kept at a temperature from 0°–150° C. (depending on the boiling point of the solution). The system is purged with oxygen before and during the reaction. The desired concentration of chlorine in the solution is obtained by feeding chlorine along with the oxygen prior to initiating the reaction. In the presence of chlorine, the reaction is initiated when the lamp (surrounded by a Pyrex ® sleeve to filter out radiation of wavelength less than 280 nm) is turned on. Additional chlorine may be fed continuously or in portions during reaction. Product is analyzed by Gas Chromatograph (GC), Ultraviolet spectrometry or GC/Mass Spectrometry during and/or after the reaction is complete. Little or no etching of the glass reactor is observed and the desired acid chloride is obtained. However, when the reaction is carried out without the Pyrex ® sleeve surrounding the light source, considerable etching of the glass equipment occurs with the concomitant formation of numerous side-product, i.e., by-products such as HF, phosgene and F-113a.

The reaction is carried out in the liquid phase and therefore the temperature is kept below the boiling point of the solution. It is advantageous to use a solvent which is inert and from which the produced acid chloride may be easily removed by distillation so that the solvent can be recycled. Depending on the boiling point and properties of the starting material it may be desirable to use the starting material as the solvent.

Solvents which are useful are those which are inert to the reaction conditions (chlorine and oxygen in the presence of light). Typical solvents are perfluorocarbons, chlorofluorocarbons such as $CCl_2F_2$, perfluoropolyethers such as Krytox® fluids, perfluorinated cyclic ethers such as FC-75 (perfluoro-2-butyltetrahydrofuran) and the perhaloacid chloride reaction products. In addition, the material to be oxidized may be used as a solvent when present in excess.

As a light source any high or medium pressure mercury vapor lamp adapted to fit the reactor system can be used.

The temperature of the reaction can range from 0°–150° C. with 10°–50° C. being the preferred range depending on the reactivity of the compound to be oxidized and the rate of the reaction. The lowest temperature giving a satisfactory reaction rate is preferred. While the higher temperature increase the reaction rate, they can cause undesirable by-product formation.

The chlorine concentration of the solution is maintained between 0.001 to 0.4M depending on the compound being oxidized, the rate of the desired reaction and the rate of side reactions, mainly chlorination. Compounds having a terminal —$CH_2Cl$ group generally need a higher concentration (>0.10M) of chlorine since chlorine serves both as a reagent and an initiator. Compounds containing a terminal —$CHCl_2$ group generally require a lower concentration (<0.02M) of chlorine. The chlorine acts to produce a controlled source of free radicals in the presence of the lower energy light (>280 nm) and thus minimizes by-product HF formation by the photodecomposition of the acid chloride product. The oxygen may be added as a pure gas or in a diluted form using inert gases such as helium, or nitrogen. Purified air may also be used.

Examples of compounds of the formula $M(CF_2)_nCH_xCl_y$ which can be used in this process include $CF_3CHCl_2$, $CF_3CH_2Cl$, $CF_3CF_2CH_2Cl$, $CF_3CF_2CHCl_2$, $ClCF_2CH_2Cl$, $ClCF_2CF_2CHCl_2$, $CF_3CF_2CF_2CF_2CH_2Cl$. This process is particularly useful for the oxidation of compounds wherein x=1 and in particular for the production of trifluoroacetyl chloride from 1,1-dichloro-2,2,2-trifluoroethane (HCFC-123). The starting materials of the general formula $M(CF_2)_nCH_xCl_y$ are known in the art or may be prepared by existing synthetic methods.

EXAMPLES

The following examples serve to illustrate the invention, but are not intended to limit the scope of the invention. All analyses in the following examples were by gas chromatography (GC) using a Hewlett-Packard Series II 5890 instrument coupled with a 3393A integrator, ultraviolet spectrometry using a Hewlett Packard 8452A Diode-Array UV/VIS Spectrophotometer or GC/mass spectrometry (GC/MS) using a Finnigan SP5100 GC/MS. For the GC and GC/MS analyses a 105 m×0.32 mm RTX-1 (Restek Corp., Bellefonte, PA) capillary column was used with a thermal conductivity detector. A temperature program of 40° C. (15 min hold), heating 16° C./min to 200° C. (10 minute hold), and heating 50° C./min to 250° C. (10 minute hold) was employed.

EXAMPLE 1

The reaction was carried out in a 1.6 liter glass annular reactor having a water-cooled double-walled immersion quartz light-well containing a 450 W medium pressure mercury vapor lamp. A Pyrex® sleeve was placed around the lamp to filter out radiation of wavelength less than 280 nm. The reactor is charged with liquid 1,1-dichloro-2,2,2-trifluoroethane until it was full. This solution was maintained around 15° C. during entire operation. The solution was purged with oxygen at 80 cc/min for 1.5 hours, followed by the addition of chlorine until the concentration of chlorine in the solution was 0.0033M. The lamp was turned on and oxygen was fed at the rate of 80 cc/min for 3 hours. Additional chlorine was occasionally fed into the solution so as to maintain an adequate reaction rate. The chlorine concentration of the solution was not allowed to rise above 0.0035M during reaction. The trifluoroacetyl chloride production rate and chlorine concentration of the solution were monitored by an on-line UV/VIS spectrophotometer. The product was then analyzed by UV/VIS spectroscopy and Gas Chromatography respectively. Trifluoroacetyl chloride (0.7 mole) in 99.0% purity was obtained. No etching of the light well or reactor was observed.

COMPARISON EXAMPLE

In a similar reaction to Example 1, but without the Pyrex® sleeve and at a temperature of about 25° C., trifluoroacetyl chloride (0.8 mole) in 81% purity was obtained. The major impurities were $CF_3CCl_3$ (4%), $CF_3CCl_2CCl_2CF_3$ (13.9%), phosgene (0.4%), and trifluoroacetic acid (0.4%). Considerable etching of the light well and reactor was observed.

EXAMPLE 2

The procedure of Example 1 was repeated using a 10 ml of 1,1-dichloro-2,2,3,3,3-pentafluoropropane, $CF_3CF_2CHCl_2$, dissolved in 900 ml of Krytox® perfluoropolyether. In the presence of 0.0037M of chlorine and two hours reaction time, 0.007 mole of pentafluoropropionyl chloride with 99.0% purity was obtained. No etching of the light well or reactor was observed.

EXAMPLE 3

The procedure of Example 2 was repeated using 10 ml of 1-chloro-2,2,3,3,3-pentafluoropropane, $CF_3CF_2CH_2Cl$, as starting material. In the presence of 0.15M of chlorine, production of pentafluoropropionyl chloride (60%) and pentafluoropropionaldehyde (40%) was determined by GC/mass. No etching of the light well or reactor was observed.

What is claimed is:

1. In a liquid phase process for the preparation of ω-haloperfluoroacid chlorides by the photo oxidation of compounds of the formula $M(CF_2)_nCH_xCl_y$ wherein M=F or Cl; n=1–10, x=1 or 2 and x+y=3; the improvement comprising conducting the photo oxidation using light wavelengths >280 nm in the presence of chlorine.

2. A process for preparing trifluoroacetyl chloride by the liquid phase photo oxidation of 1,1-dichloro-2,2,2-trifluoroethane using ultraviolet light of wavelengths >280 nm in the presence of chlorine.

3. The process of claim 1 or claim 2 wherein the reaction is carried out in a solvent.

4. The process of claim 3 wherein x=2 and the chlorine concentration of the solution is between 0.1 to 0.4M.

5. The process of claim 3 wherein x=2 and the chlorine is an initiator and a reagent.

6. The process of claim 3 wherein x=1 and the chlorine concentration of the solution is between 0.001 to 0.02M.

* * * * *